United States Patent
Hoersch et al.

(10) Patent No.: US 6,406,894 B1
(45) Date of Patent: *Jun. 18, 2002

(54) PROCESS FOR PREPARING POLYVALENT AND PHYSIOLOGICALLY DEGRADABLE CARBOHYDRATE-CONTAINING POLYMERS BY ENZYMATIC GLYCOSYLATION REACTIONS AND THE USE THEREOF FOR PREPARING CARBOHYDRATE BUILDING BLOCKS

(75) Inventors: Brigitte Hoersch, Kriftel; Michael Ahlers, Mainz; Gerhard Kretzschmar, Eschborn; Eckart Bartnik, Wiesbaden; Dick Seiffge, Mainz-Kostheim, all of (DE)

(73) Assignee: Glycorex AB, Lund (SE)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

This patent is subject to a terminal disclaimer.

(21) Appl. No.: 08/989,136

(22) Filed: Dec. 11, 1997

Related U.S. Application Data

(63) Continuation of application No. 08/562,826, filed on Nov. 27, 1995, now abandoned, which is a continuation-in-part of application No. 08/165,805, filed on Dec. 13, 1993, now Pat. No. 5,470,843.

(30) Foreign Application Priority Data

Dec. 11, 1992 (DE) .......................................... 42 41 829
Jun. 16, 1994 (DE) .......................................... 44 20 943

(51) Int. Cl.$^7$ ........................... C12P 19/18; C07H 7/00; C07H 3/06
(52) U.S. Cl. .................. 435/97; 435/100; 435/101; 536/4.1; 536/20; 536/21; 536/17.2; 536/18.5; 536/18.7; 536/55; 536/55.1; 536/55.2; 536/55.3; 536/102; 536/123.1; 536/124; 536/126; 525/32.2
(58) Field of Search ........................... 435/97, 100, 101; 536/55, 55.1, 55.2, 55.3, 123.1, 126, 4.1, 20, 21, 17.2, 18.5, 18.7, 45, 102, 124; 525/32.2

(56) References Cited

U.S. PATENT DOCUMENTS

| | | | |
|---|---|---|---|
| 4,804,542 A | 2/1989 | Fischer et al. | 424/456 |
| 4,834,248 A | 5/1989 | Lee | 211/13 |
| 4,835,248 A | 5/1989 | Bader et al. | 528/328 |
| 4,925,796 A | 5/1990 | Bergh et al. | 435/97 |
| 5,059,654 A | 10/1991 | Hou et al. | 525/54.2 |
| 5,219,926 A | 6/1993 | Lindman et al. | 525/54.1 |
| 5,254,676 A | 10/1993 | Sabesan | 536/4.1 |
| 5,369,017 A | 11/1994 | Wong et al. | 435/68.1 |
| 5,462,990 A | 10/1995 | Hubbell et al. | 525/54.1 |
| 5,470,843 A | 11/1995 | Stahl et al. | 514/61 |

FOREIGN PATENT DOCUMENTS

| | | |
|---|---|---|
| EP | 0 089 938 B1 | 9/1983 |
| EP | 0 089 939 | 9/1983 |
| EP | 0 601 417 A2 | 6/1994 |
| WO | WO 91/19501 | 12/1991 |
| WO | WO 91/19502 | 12/1991 |
| WO | WO 92/02527 | 2/1992 |
| WO | WO 92/22563 | 12/1992 |
| WO | WO 92/22565 | 12/1992 |
| WO | WO 92/22661 | 12/1992 |

OTHER PUBLICATIONS

Unverzagt et al, J. Am. Chem. Soc. 112: 9308–9309 (1990).*

T. Feizi et al., "Carbohydrates as antigenic determinants of glycoproteins", *Biochem. J.*, 245:1–11 (1987).

Stults et al., "Glycosphingolipids: Structure, Biological Source, and Properties", *Methods in Enzymology* 179:167 (1989).

S. Hakomori, "Aberrant Glycosylation in Tumors and Tumor–Associated Carbohydrate Antigens", *Adv. Cancer Res.* 52:257 (1989).

Bevilacqua et al., "Endothelial Leukocyte Adhesion Molecule–1: An Inducible Receptor for Neutrophils Related to Complement Regulatory Proteins and Lectins", *Science*, 243:1160–1165 (1989).

Connolly et al., "Binding and Endocytosis of Cluster Glycosides by Rabbit Hepatocytes", *J. Biol. Chem.* 257(2):939–945 (1982).

Spaltenstein et al., "Polyacrylamides Bearing Pendant α–Sialoside Groups Strongly Inhibit Agglutination of Erythrocytes by Influenza Virus", *J. Am. Chem. Soc.*, 113:686–687 (1991).

(List continued on next page.)

Primary Examiner—Francisco Prats
(74) Attorney, Agent, or Firm—Foley & Lardner

(57) ABSTRACT

A process for preparing polyvalent, physiologically degradable carbohydrate-containing polymers by enzymatic glycosylation reactions is described. The carbohydrate-containing polymers thus prepared may be used for preparing carbohydrate building blocks. The polyvalent carbohydrate-containing polymers of the invention cause no intolerance reactions in vivo, either in their intact form or in the form of degradation products. The carbohydrate side chain of the carbohydrate-containing polymer is assembled by enzymatic glycosylation reactions in homogeneous aqueous buffer systems directly on a biodegradable polymer. The yields of the glycosylation reaction are significantly improved over known processes, and are often quantitative. This also provides a significant increase in the loading densities. A process for preparing free oligosaccharides by means of the carbohydrate-containing polymers of the invention is also described.

17 Claims, No Drawings

OTHER PUBLICATIONS

N. Yamazaki et al., "Studies on Carbohydrate Binding Proteins Using Liposome–Based Systems–I,—Preparation of Neoglycoprotein–Conjugated Liposomes and the Feasibility of Their Use as Drug Targeting Devices", *Int. J. Biochem.* 24(1):99–104 (1992).

R. Rathi et al., "N–(2–Hydroxypropyl) methacrylamide Copolymers Containing Pendant Saccharide Moieties: Synthesis and Bioadhesive Properties", *J. Polym. Sci.*, 29:1985–1902 (1991).

S. Nishimura et al., "Synthetic Glycoconjugates 2.[1] n–Pentenyl Glycosides and Convenient Mediators for the New Types of Glycoprotein Models", *Macromolecules* 24:4236–4241 (1991).

Pitha and Kusiak, "Interaction of Macromolecular Drugs with Beta–Adrenoceptors", *Annals New York Academy of Sciences* 446:249–257 (1985).

Nishimura et al., "Chemoenzymic Preparation of A Glyconjugate Polymer Having A sialyloligosaccharide: Neu5Aca(Galβ(1→4)G1cNAc", Biochem. Biophys. Res. Comm. 199:249–253 (1994).

Zehavi, "Innovation Perspect. Solid Phase Synthesis Collect. Paper", *Int. Symp.* 1990: 389.

Zehavi, "Polymers as Supports for Enzymic Oligo–And Polysaccharide Synthesis," *Reactive Polymers*, 6: 189 (1987).

Zehavi, "Enzymic Synthesis of Oligosaccharides on a Polymer Support. Light–Sensitive, Substituted Polyacrylamide Beads," *Carbohydrate Research.* 124: 23 (1983).

Wong et al., "Ligand Recognition by E–Selectin: Analysis of Confirmation and Activity of Synthetic Monomeric and Bivalent Sialyl Lewis X Analogs," *J. Amer. Chem. Soc.* 115:7549 (1993).

Danishefsky et al., "A strategy for the Solid–Phase Synthesis of Oligosaccharides," *Science*, 260: 1307 (1993).

Douglas et al., "Polymer–Supported Solution Synthesis of Oligosaccharides," *J. Am. Chem. Soc.* 113:5095 (1991).

Zehavi et al., "Oligosaccharide Synthesis on a Light–Sensitive Solid Support. I. The Polymer and Synthesis of Isomaltose (6–0–α–D–Glucopyranosyl–D–glucose)," *J. Am. Chem. Soc.* 95:5673 (1973).

Nunez and Barker, "Enzymatic Synthesis and Carbon–13 Nuclear Magnetic Resonance Conformational Studies of Disaccharides Containing β–D–Galactopyranosyl and β–D [1–$^{13}$C]Galactopyranosyl Residues, "*Biochemistry* 19:489 (1980).

Zehavi et al., "Enzymic Synthesis of Oligosaccharides on a Polymer Support Light–Sensitive, Water–Soluble Substituted Poly(Vinyl Alcohol),"*Carbohydrate Res.* 128:160 (1984).

Zehavi et al., "Enzymic Glycosphingolipid Synthesis on Polymer Supports," *Glycoconjugate J.* 7:229 (1990).

Zehavi et al., Enzymic Synthesis of Oligosaccharides on an α–Chymotrypsin–Sensitive Polymer.

O–(β–D–Galactoyranosyl)–(1→4k)–D–Glucopyranose, *Carbohydrate Res.* 133:339 (1984).

Wong et al., "Solid–Phase Chemical–Enzymatic Synthesis of Glycopeptides and Oligosaccharides," *J. Amer. Chem. Soc.* 116:1135 (1994).

Ichidawa et al., *J. Am. Chem. Soc.*, 114:9283–9298, (1992).

Palcic et al., *Carb. Res.*, 190:1–11, (1989).

Ball et al. *J. Am. Chem. Soc.*, 114:5449–5451, (1992).

* cited by examiner

PROCESS FOR PREPARING POLYVALENT AND PHYSIOLOGICALLY DEGRADABLE CARBOHYDRATE-CONTAINING POLYMERS BY ENZYMATIC GLYCOSYLATION REACTIONS AND THE USE THEREOF FOR PREPARING CARBOHYDRATE BUILDING BLOCKS

This application is a continuation of application Ser. No. 08/562,826, filed Nov. 27, 1995, now abandoned, which is in turn a continuation-in-part of application Ser. No. 08/165,805 filed Dec. 13, 1993 now U.S. Pat. No. 5,470,843, and which claims benefit to PCT/EP95/02285, filed Jun. 13, 1995.

BACKGROUND OF THE INVENTION

This invention is directed to a process for using enzymatic glycosylation reactions to prepare polyvalent carbohydrate-containing polymers. These carbohydrate-containing polymers do not cause intolerance reactions in vivo, either in their intact state, or in the form of metabolites produced by physiological degradation processes. The process may also be used for preparing carbohydrate building blocks.

The role of carbohydrates as information carriers in physiologically relevant recognition processes has recently been a subject of intense study. The presence of carbohydrates as ligands on cell surfaces allows them to play, via binding to specific carbohydrate receptors, a crucial part in intercellular communication and in intercellular recognition processes. Carbohydrate ligands on cell surfaces act as recognition elements for, for example, viruses, bacteria, toxins and lectins. Carbohydrates therefore play a crucial role part in, inter alia, bacterial and viral infections, and in the initiation of inflammatory processes such as rheumatoid arthritis, allergies, post-infarct syndrome, shock, stroke and sepsis. Recent investigations have shown that during inflammatory processes the interaction between a carbohydrate ligand and a selectin expressed by endothelial cells mediates adhesion of leukocytes to inflammatory foci. Carbohydrate ligands that are particularly important for cell adhesion are sialylated and/or fucosylated carbohydrates such as sialyl-Lewis X and sialyl-Lewis A.

Therapeutic approaches to treating inflammatory disorders using free oligosaccharides to block the binding of natural ligands to receptors have been largely unsuccessful due to the low affinities observed between the receptor and the oligosaccharide (e.g. the dissociation constant, $K_D \sim 10^{-4}$ M for the interaction between a monovalent galactoside and the corresponding lectin, D. T. Connolly et al., *J. Biol. Chem.* 257, 939, (1982)). These low affinities lead to a requirement for administering very high dosages of carbohydrate. Some divalent structures have, however, been show to have somewhat better binding affinities for a particular receptor. See. for example, Wong et al., *J. Amer. Chem. Soc.* 115:7549 (1993) and U.S. Pat. No. 5,254,676.

It has been shown that increased interaction between. receptor and ligand can be achieved by coupling a plurality of ligands to a surface. For example, the ligand-receptor interaction between neuraminic acid and the viral protein hemagglutinin is significantly enhanced by coupling multiple carbohydrate moieties to a polymer. Thus the $K_D$ for the monovalent interaction is $2 \times 10^{-4}$ M, and the $K_D$ for the polyvalent interaction is $3 \times 10^{-7}$ M. Spaltenstein et al., *J. Amer. Chem. Soc.* 113:686 (1991).

Surfaces used to date have been liposomes (Yamazaki, *Int. J. Biochem.* 24:99 (1991); WO 91/19501; WO 91/19502), polyacrylamides (Rathi et al.,*J. Polym. Sci.*: Part A: *Polym. Chem.* 29:1895 (1991), Nishimura. et al., *Macromolecules* 24:4236 (1991)), and polylysine or sulfated polysaccharides. These polyvalent structures have the disadvantage either of having only low stability in vivo or of not being tolerated in vivo due to degradation to toxic metabolites. In the case of polylysine or sulfated polysaccharides non-specific interactions with cell surface structures are also observed. European Published Patent Specifications EP 0 089 938, EP 0 089 939 and EP 0 089 940 describe carbohydrate compounds of varying chain length that are identical to ligands located on cell surfaces or receptors located on microorganisms. These carbohydrate compounds are intended to block receptors located on the microorganisms in vitro and in vivo in order to diagnose and treat diseases. The carbohydrate compounds in these cases may be coupled to a carrier, which may be used, inter alia, to produce antibodies. Similarly, WO 92/02527 discloses an oligosaccharide building block coupled to a solid carrier that may be used to diagnose inflammatory processes. The solid carrier is inert toward physiological systems and is thus not physiologically degraded.

In contrast, EP 0 601 417 A2, which is hereby incorporated by reference in its entirety, discloses a physiologically degradable polymer-based carbohydrate receptor blocker that carries oligosaccharide building blocks on the polymer surface. Improved pharmaceutical activity is obtained by enhanced interaction of the carbohydrate building blocks, which are present polyvalently on the polymer surface, with receptors, and by blocking specific structures. The carbohydrate receptor blocker is physiologically well tolerated, and has a preferred molecular weight of less than about 70 kD.

The physiologically tolerated and physiologically degradable polymer-based carbohydrate receptor blocker disclosed in EP 0 601 417 A2 has the following structure:

carbohydrate side chains—spacer—hydrophilic biodegradable polymer—potentiator (optional), where the carbohydrate side chains consist of 1 to naturally occurring, identical or different monosaccharide units that are coupled via one or more bifunctional spacers of natural or synthetic origin to a hydrophilic, biodegradable polymer. The hydrophilic, biodegradable polymer optionally is linked to a potentiator consisting of one or more groups with hydrophobic, hydrophilic or ionic properties, or the potentiator is a crosslinker or enhances solubility.

The carbohydrate portion of the receptor blocker disclosed in EP 0 601 417 A2 may comprise, for example, the following sugar residues:

Galβ1-4GlcNAc-;
Galβ1-3GlcNAc-;
SAα2-6Galβ1-4GlcNAc-;
SAα2-3Galβ1-4GlcNAc-;
SAα2-3Galβ1-3GlcNAc-;
Galβ1-4(Fucα1-3)GlcNAc-;
Galβ1-3(Fucα1-3)GlcNAc-;
SAα2-3Galβ1-3(Fucα1-4)GlcNAc-;
SAα2-3Galβ1-4(Fucα1-3)GlcNAc-.

Other examples of preferred embodiments of the carbohydrate portion are: sialyl-Lewis X, sialyl-Lewis A, VIM-2 and the following blood-group determinants: Lewis A, B, X, Y and A type[1], A type[2], B type[1], B type[2] and H type[1] and H type[2] (see Lemieux, *Chem. Soc. Rev.*, (1978) p. 423 and *Chem. Soc. Rev.*, (1989) p. 347). Particularly preferred embodiments of the carbohydrate portion are sialyl-Lewis X, sialyl-Lewis A or VIM-2.

The formula of sialyl-Lewis X is: NeuNAα2-3Gal1-4-(Fucα1-3)GlcNAc. The formula of sialyl-Lewis A is: NeuNAα2-3Galβ1-3-(Fucα1-4)GlcNAc. The formula of VIM-2 is: NeuNAα2-3Galβ1-4GlcNAcβ1-3Galβ1-4(Fucα1-3)GlcNAc.

EP 0 601 417 A2 discloses a process for the preparation of the carbohydrate receptor blocker that is suitable for use on a laboratory scale. The carbohydrate receptor blocker accordingly can be synthesized only in milligram to gram quantities. The non-carbohydrate intermediates necessary for the synthesis, i.e., the hydrophilic biodegradable polymer, the bifunctional spacer and the potentiator can, however, be prepared in gram to kilogram amounts.

The limitation in the scale of the overall synthesis of the blocker is due to the synthetic schemes necessary to prepare the carbohydrate portion of the blocker. These schemes can only readily yield amounts of carbohydrate up to one gram. Known synthetic schemes for the preparation of oligosaccharides involve steps that do not proceed with a quantitative yield, and the product mixture obtained after each reaction must be purified by silica gel chromatography. This purification process is generally too costly and elaborate for preparing industrial quantities of material, and is used at the most for purifying final products or valuable intermediates. Additionally, oligosaccharide synthesis frequently uses heavy metal compounds as reagents, which is problematic for subsequent regulatory approval of the blockers as pharmaceutical products, due to possible heavy metal contamination.

In the process described in EP 0 601 417 A2, the required oligosaccharide is linked to the biodegradable polymer by means of a spacer only after the oligosaccharide has been assembled via a large number of chemical and/or chemoenzymatic synthetic stages. These syntheses are very lengthy and difficult because of the well known problems associated with assembly of oligosaccharides, for example, use of protective groups, anomer formation, poor yields of glycosylation reactions, non-stereoselective glycosylation, and the requirement for multiple step reaction schemes.

In view of the problems associated with consecutive reaction and purification steps in the chemical and/or chemoenzymatic synthesis of carbohydrate building blocks, some solid-phase syntheses have recently been proposed. In contrast to the established solid-phase syntheses of oligonucleotides and peptides, the chemical synthesis of oligosaccharides on polymeric solid phases is very difficult owing to the large number of functional groups and the need for stereoselective formation of the glycosidic linkage. Danishefsky et al., (*Science*, 260:1307 (1993)) linked 3,4-protected glycals via silyl ether linkages to a polystyrene copolymer. The latter is activated as an epoxide and can be linked to further glycal acceptors to give the oligosaccharide. Douglas et al., (*J. Am. Chem. Soc.* 113:5095 (1991)) described the synthesis of di- and trisaccharides on a PEG-bound glucose unit. Zehavi (*J. Am. Chem. Soc.* 95:5673 (1973)) used a photosensitive styrene/divinylbenzene copolymer as the polymeric solid phase, where the protected oligosaccharide is cleaved from the polymer by irradiation.

The disadvantages of chemical solid-phase synthesis of oligosaccharides include:

glycosylation reactions are often incomplete;

only a few donor or acceptor glycosylation building blocks are suitable; and the need for protecting groups appropriate for the particular reaction.

These disadvantages of the chemical synthesis of oligosaccharides on polymeric matrices can be avoided by using enzymatic glycosylation. In this approach reactions take place without protective groups and with stereospecificity. Additionally, enzymatic glycosylation can be employed widely owing to the availability of large number of available glycosyltransferases and nucleotide-activated sugars as glycosyl donors.

As long ago as 1980, Nunez and Barker (*Biochemistry* 19:499 (1980)) described the enzymatic galactosylation of N-acetylglucosamine linked to agarose via a hexanolamine spacer. Very large amounts of galactosyltransferase enzyme were required, however. Zehavi has described enzymatic galactosylation using galactosyltransferase on photosensitive polymers, where the polymers were either soluble or insoluble in water. Transfer yields were very low, ranging from less than 1% to a maximum of 36% (Zehavi et al., *Carbohydrate Res.* 124:23 (1983), Zehavi et al., *Carbohydrate Res.* 128:160 (1984), Zehavi, *Reactive Polymers* 6:189 (1987), Zehavi et al., *Glycoconjugate J.* 7:229 (1990) and Zehavi, "Innovation Perspect. Solid Phase Synthesis Collect. Paper", *Int. Symp.* 1990:389). The resulting disaccharide on the polymer was cleaved from the polymer by the action of light, or by an enzyme (Zehavi et al., *Carbohydrate Res.* 133:339 (1984)).

Nishimura et al., (*Biochem. Biophys. Res. Comm.* 199:249–254 (1994)) described the enzymatic preparation of a water-soluble polyacrylamide with 3'-sialyl-N-acetyllactosamine side chains, using stepwise enzymatic glycosylation of a water-soluble, N-acetylglucosamine-carrying polyacrylamide. Only low loading densities were achieved, however, with low overall yields.

A more recent paper by Wong et al., (*J. Amer. Chem. Soc.* 116:1135 (1994)) describes the enzymatic synthesis of oligosaccharides on a modified silica gel. Owing to the insolubility of the silica gel in the aqueous buffers needed for the enzymatic carbohydrate synthesis and the low loading density of the GlcNAc building block linked via a peptide, only low glycosylation yields were achieved in all three reaction steps. Thus, after enzymatic cleavage of the peptide anchor, product mixtures containing only 20% of the required product and 45% of the precursor were obtained.

WO 92/22661, WO 92/22565 and WO 92/22563 propose enzymatic glycosylations with a sialyltransferase of disaccharides linked to an "unnatural carrier" (artificial carrier). An "unnatural carrier" is, as a rule, a high or low molecular weight carrier with antigenic properties, for example bovine serum albumin, KLH, HSA, diphtheria or tetanus toxin, etc., or a solid carrier that is inert toward physiological systems.

It is apparent, therefore, that an efficient method for preparing a polyvalent, physiologically tolerated and physiologically degradable carbohydrate-containing polymer is greatly to be desired. In particular, it is greatly desirable to synthesize the carbohydrate-containing polymer by high yield enzymatic glycosylation reactions.

SUMMARY OF THE INVENTION

It is therefore an object of the present invention to provide a process for preparing polyvalent carbohydrate-containing polymers that are physiologically degradable in vivo. The polyvalent carbohydrate-containing polymers thus prepared comprise a hydrophilic, biodegradable polymer unit, a disaccharide or oligosaccharide unit, and a bifunctional spacer linking the disaccharide or oligosaccharide units to the biodegradable polymer unit.

It is another object of the invention to provide a process for the diagnosis, therapy or prophylactic treatment of bacterial or viral infections, post-infarct syndrome, shock, stroke, acute and chronic organ rejection, vasculitis, inflammatory disorders, rheumatoid arthritis, metastatic tumors and shock lung, comprising the use of a carbohydrate-containing polymer that is physiologically degradable in vivo, where the carbohydrate-containing polymer comprises a hydrophilic, biodegradable polymer unit, a disaccharide or oligosaccharide unit, and a bifunctional spacer linking the disaccharide or oligosaccharide units to the biodegradable polymer unit.

It is yet another object of the invention to use the carbohydrate-containing polymer prepared according to the methods of the invention for preparing free oligosaccharides.

In accomplishing the foregoing objects of the invention, there has been provided, in accordance with one aspect of the current invention, a process to assemble the carbohydrate portion of the carbohydrate-containing polymer by enzymatic glycosylation reactions in aqueous buffer systems in a homogeneous phase directly onto a biodegradable polymer. The yields of the glycosylation reactions are greatly improved in comparison with the yields of known processes. The process comprises the steps of: (a) covalently linking a monosaccharide or oligosaccharide unit to a spacer to form a monosaccharide or oligosaccharide-spacer complex; (b) covalently linking the monosaccharide or oligosaccharide-spacer complex to a hydrophilic, biodegradable polymer unit to form an acceptor unit; and (c) coupling a monosaccharide donor unit to the acceptor unit by enzymatic glycosylation. In accordance with another aspect of the invention the process comprises the steps of: (a) covalently linking the hydrophilic, biodegradable polymer unit to the spacer to form a biodegradable polymer-spacer complex; (b) covalently linking the biodegradable polymer-spacer complex to a monosaccharide or oligosaccharide unit to form an acceptor unit; and (c) coupling a monosaccharide donor unit to the acceptor unit by enzymatic glycosylation.

In accordance with a further aspect of the invention, there has been provided a process where the enzymatic glycosylation of the acceptor unit takes place in a homogeneous aqueous phase, preferably using nucleotide-activated carbohydrates as the monosaccharide donor units. In another preferred embodiment the glycosylation reaction is catalyzed by at least one glycosyltransferase, at between about pH 6.0 and about pH 8.5. Preferably about 0.01 to 10 units of the glycosyltransferase are used, and the enzymatic glycosylation is carried out at a temperature between about 10° C. and about 40° C. for between about 1 to about 5 days.

In accordance with another aspect of the invention, alkaline phosphatase is added to the reaction medium when the monosaccharide donor unit is added in equimolar amount or in excess.

In accordance with still another aspect of the invention, the hydrophilic biodegradable polymer unit is selected from the group consisting of a polycarbonate, polyester, polyamide, polyanhydride, polyiminocarbonate, polyorthoester, polydioxanone, polyphosphazene, polyhydroxycarboxylic acid, polyamino-acid and a polysaccharide. The polymer preferably is a polyamino-acid having a molecular weight up to about 70 kD, wherein the polyamino-acid is in polyamide or polyanhydride form. The polyamino-acid is preferably selected from the group consisting of poly-α,β-(2-hydroxyethyl)-D,L-aspartamide, poly-D,L-succinimide, polyglutamate, poly-L-lysine methyl ester fumaramide and a copolymer of these polyamino-acids.

In accordance with a still further aspect of the invention, the acceptor unit has the formula: (monosaccharide or oligosaccharide)—O—{$Q^1$—$(CH_2)p$-$Q^2$}$_r$(polymer unit), wherein $Q^1$ is —$CH_2$ or —CO—, $Q^2$ is —NH or —CO—NH—, p is 1–6, and r is 1 or 2. The linkages connecting the spacer to the monosaccharide or oligosaccharide unit and to the biodegradable polymer unit are preferably formed by reactions selected from the group consisting of alkylation, reductive alkylation, acylation and addition onto a double bond.

In accordance with yet another aspect of the invention, the disaccharide or oligosaccharide unit of the carbohydrate-containing polymer is selected from the group consisting of: SAα2-6Galβ1-4GlcNAc-; SAα2-3Galβ1-4GlcNAc-; SAα2-3Galβ1-3GlcNAc-; Galβ1-4(Fucα1-3)GlcNAc-; Galβ1-3(Fucα1-3)GlcNAc-; SAα2-3Galβ1-3(Fucα1-4) GlcNAc-; SAα2-3Galβ1-4(Fucα1-3)GlcNAc-, sialyl-Lewis X, sialyl-Lewis A, VIM-2, Lewis A, Lewis B, Lewis X, Lewis Y, Lewis A type$^1$, Lewis A type$^2$, Lewis B type$^1$, Lewis B type$^2$, Lewis H type$^1$ and Lewis H type$^2$.

In accordance with a still further aspect of the invention, the nucleotide-activated carbohydrate is preferably selected from the group consisting of: UDP-galactose, UDP-glucose, UDP-N-acetylglucosamine, UDP-N-acetyl-galactosamine, UDP-glucuronic acid, CMP-neuraminic acid, GDP-fucose, GDP-mannose, dTDP-glucose and dUDP-galactose. The glycosyltransferase is preferably selected from the group consisting of: β-1,4-galactosyltransferase, Gal-β-1-4-GlcNAc α-2-6-sialyltransferase, Gal-β-1-3-GalNAc α-2-3-sialyltransferase, Gal-β-1-3(4)-GlcNAc α-2-3-sialyltransferase, GalNAc α-2-6-sialyltransferase, N-acetylglucosaminyltransferases, α-1-3-fucosyltransferase, α-1-2-fucosyltransferase, α-3/4-fucosyltransferase, and α-1-2-mannosyltransferase. The disaccharide or oligosaccharide unit preferably contains 2–20 monosaccharide units.

Other objects, features and advantages of the present invention will become apparent from the following detailed description. It should be understood, however, that the detailed description and the specific examples, while indicating preferred embodiments of the invention, are given by way of illustration only, since various changes and modifications within the spirit and scope of the invention will become apparent to those skilled in the art from this detailed description.

DETAILED DESCRIPTION OF THE INVENTION

The present invention provides a process for preparing polyvalent, physiologically tolerated and physiologically degradable carbohydrate-containing polymers that act as receptor blockers. The process is distinguished by using enzymatic glycosylation reactions to assemble the carbohydrate portion of the receptor blocker. These reactions take place directly on the soluble biodegradable polymer in a homogeneous phase in aqueous buffer systems. The yields of the glycosylation reaction are greatly improved in comparison with the yields of known processes and, as a rule, take place quantitatively. The loading densities of oligosaccharide on the polymer are also greatly increased over those achieved in the prior art. The carbohydrate-containing polymers prepared according to the methods of the invention may also be used for preparing the free oligosaccharides.

The physiologically tolerated and physiologically degradable carbohydrate-containing polymer comprises:
  a) a hydrophilic, biodegradable polymer unit;
  b) at least one di- or oligosaccharide unit; and
  c) at least one bifunctional spacer by which the di- or oligosaccharide units are linked to the polymer unit.

The carbohydrate-containing polymer is prepared by a process wherein an acceptor is prepared by covalently linking together a mono- or oligosaccharide, a spacer and a hydrophilic biodegradable polymer, followed by attaching one or more additional monosaccharide units by enzymatic glycosylation. The spacer can first be linked to the mono- or oligosaccharide, followed by coupling to the polymer, or the spacer can first be linked to the polymer followed by coupling to the mono- or oligosaccharide. The enzymatic glycosylation reaction takes place stereoselectively and with surprisingly high yields directly on the polymer and can, because each glycosylation step takes place essentially quantitatively, be repeated as often as necessary with any desired donors. The process preferably uses nucleotide-activated carbohydrates as donors and one or more glycosyltransferases as the enzyme in the glycosylation reactions.

The aqueous medium is preferably a buffer system suited to the particular glycosyltransferase, and the buffer system preferably has a concentration of 0.01 M to 1 M. The buffer preferably contains any cations necessary for activating the particular glycosyl-transferase, for example, $Mn^{2+}$. The pH of the glycosylation reaction is preferably between about 6.0 and about 8.5, more preferably between about 6.5 and about 8.0, and most preferably between about 7.0 and about 7.5.

When the donor is added in approximately equimolar amounts or in excess, alkaline phosphatase is preferably added to the reaction medium. Between about 0.01 to about 10 units of the glycosyltransferase are added to the reaction mixture. The glycosylation is carried out at a temperature between about 10° C. to about 40° C., preferably at about 20° C. to about 37° C., even more preferably at about 25° C. to about 37° C., for about 1 to 5 days.

The invention is explained in detail hereinafter:

1. SYNTHESIS OF THE ACCEPTOR FOR THE ENZYMATIC GLYCOSYLATION REACTION

The acceptor for the enzymatic glycosylation reaction consists of a mono- or oligosaccharide which is covalently linked via a spacer to a biodegradable hydrophilic polymer. The polymer can be provided with a potentiator comprising one or more groups with hydrophobic, hydrophilic or ionic properties, or the potentiator is a crosslinker or enhances solubility. The acceptor is synthesized by methods known to the skilled artisan. The individual building blocks of the acceptor are described hereinafter.

A. Biodegradable Hydrophilic Polymer

By definition, the polymer consists of at least two identical or different monomer units that are linked together in linear or branched fashion and that may display a molecular weight distribution. The polymer is preferably a polyamino-acid linked via polyamide or anhydride linkages, with a molecular weight less than or equal to about 70 kD. The preferred minimum size of the polymer is about 2 kD in order to achieve increased residence time in the blood by comparison with low molecular weight carriers.

Preferred polyamino-acids for preparing carbohydrate-containing polymers are polyaspartamides, polysuccinimides, polyglutamates and polylysine-fumaramides. Particularly preferred polymers include, for example, poly-α,β-(2-hydroxyethyl)-D,L-aspartamide, poly-D,L-succinimide, polyglutamate, poly-L-lysine methyl ester furamamide, and copolymers thereof.

The biodegradable, hydrophilic polymer is prepared by processes known to the skilled artisan. Suitable methods are described, for example, in Elias, *Makromolekü* [Macromolecules], Volumes 1 and 2, Hüthig & Wepf Verlag, Basle, Switzerland, 1991/92 and Braun et al., *Praktikum der Makromolekularen organischen Chemie* [Practical Molecular Organic Chemistry], Hüthig Verlag 1979.

Thus, for example, poly-D,L-succinimide (PSI) is prepared by the method of Neri et al., (*J. Med. Chem.*, 16:893 (1973)) by the action of 85% phosphoric acid on aspartic acid at temperatures of 160° C.–180° C. Reaction of PSI polymer with hydroxyethylamine at room temperature or slightly elevated temperature results in poly-α,β-(2-hydroxyethyl)-D,L-aspartamide (PHEA). Alcohol groups on the PHEA can be esterified by well known methods. See, for example, U.S. Pat. No. 5,041,291. Partial reaction of PSI with ethanolamine results in corresponding copolymers. See U.S. Pat. No. 5,229,469. Basic hydrolysis of PSI leads to polyaspartic acid (in an analogous manner to that described by Giammona et al., (*Chem Pharm. Bull.* 37:2245 (1989)). In similar fashion to the reaction with hydroxyethylamine, PSI can also be reacted with other amines (see EP 0 548 794), which makes it possible to introduce additional functional groups which may act as potentiators.

Poly-L-lysine methyl ester fumaramide, can be prepared by boundary phase polycondensation of L-lysine methyl ester and fumaryl chloride. See U.S. Pat. No. 4,835,248. The methyl ester groups can be reacted directly or after partial hydrolysis and subsequent activation, for example as p-nitrophenyl ester, with the mono-, di- and oligosaccharides containing amino groups.

In an analogous way, i.e., using p-nitrophenyl esters, it is possible to prepare carbohydrate-containing polymer based on polyglutamates. See Anderson in "Macromolecules as Drugs and as Carriers for Biologically active Materials" (Ed: D. A. Tirell), NY Acad. Sci., NY, 1985, pp. 67–75.

B. Spacer

The covalent linkages between (i) the polymer and the spacer; (ii) the polymer and the covalently linked spacer/carbohydrate compound; (iii) the spacer and the covalently-linked polymer/potentiator, and (iv) the covalently-linked polymer/potentiator and the covalently linked spacer/carbohydrate compound, are formed by reaction between a reactive group and an activated group. Suitable reactions are well known to the skilled artisan, and include alkylation, reductive alkylation, acylation or addition onto a double bond. These and other suitable reactions are described in Larock, *Comprehensive Organic Transformations*, 1989, VCH Verlagsgesellschaft Weinheim).

The reactive group may be located at the terminus of the spacer or at the terminus of the covalently-linked spacer/carbohydrate compound. The activated group may be located on the polymer or on the covalently-linked polymer/potentiator compound. The activated group may be located at the end of the spacer or at the terminus of the covalently-linked spacer/carbohydrate compound. The reactive group may be located either on the polymer or on a covalently-linked polymer/potentiator compound.

The spacer preferably has the formula I:

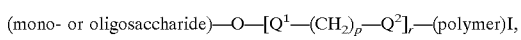

wherein

Q$^1$ is —CH$_2$ or —CO—,

Q$^2$ is —NH or —CO—NH—, p is an integer from 1 to 6 and r is 1 or 2

C. Carbohydrate Portion of the Acceptor

The carbohydrate portion of the acceptor for the enzymatic glycosylation reaction may be derived from natural sources or may be prepared chemically, chemoenzymatically, or enzymatically. Suitable natural sources for carbohydrates are well known to the skilled artisan. Processes for purifying oligosaccharides are also well known to the skilled worker.

Methods for chemical, enzymatic or chemoenzymatic synthesis of carbohydrates that bind to cell surface receptors are similarly known to one of skill in the art. Many suitable chemical syntheses are described, for example, in: *Carbohydrate Research*, Elsevier Science Publishers B.U. Amsterdam; *Journal of Carbohydrate Chemistry*, Marcel Dekker Inc. New York; Paulsen, *Angew. Chem.* 94:184 (1982) and 102:851 (1990); Schmidt *Angew. Chem.* 98:213 (1987); and Kunz. *Angew. Chem.* 98:247 (1987). Enzymatic syntheses are described in, for example: *Carbohydrate Synthesis*, ACS Symposium Series 466 (1991); Nilsson, *Applied Biocatalysis* 1991:117; David et al., *Adv. Carbohydr. Chem. Biochem.* 49:175 (1991); Ichikawa et al., *Anal. Biochem.* 202:215 (1992); Drueckhammer et al., *Synthesis* 1991:499; Toone et al., *Tetrahedron* 45:5365 (1980).

Mono- or oligosaccharides prepared in this way can be prepared either with a free reducing end or in a spacer-linked form. The spacer is introduced by processes known to the skilled worker for chemical or enzymatic glycosylation.

2. ENZYMATIC GLYCOSYLATION

The acceptor for the enzymatic glycosylation reaction, prepared as described supra, consists of a mono- or oligosaccharide covalently linked via a spacer to a biodegradable hydrophilic polymer. The polymer may optionally be provided with a potentiator. Enzymatic glycosylation of the acceptor preferably takes place in homogeneous aqueous phase, preferably using nucleotide-activated carbohydrates as donors, and glycosyltransferases as enzymes.

The acceptor is dissolved in an aqueous buffer system. The buffer is chosen as appropriate for the particular glycosyltransferase and may contain, for example, cacodylate, HEPES, PIPES, MOPS, citrate, bicarbonate, etc., at concentrations of about 0.01 M to 1 M. The buffer also contains any cations necessary for activating the particular glycosyltransferase, for example $Mn^{2+}$. The pH of the buffer is also chosen to be appropriate for a particular glycosyltransferase, and is preferably between about 6.0 and about 8.5, more preferably between about 6.5 and about 7.8, and most preferably between about 7.0 and about 7.5.

After the acceptor has been dissolved in the aqueous buffer system, the donor is added. The donor moiety is a nucleotide-activated sugar or an analog of a nucleotide-activated sugar, for example d-UDP-Glc, d-UDP-Gal, d-UDP-GlcNAc, where d-UDP is deoxyuridine diphosphate. The nucleotide-activated sugars are commercially available, for example from Sigma (St. Louis, Mo.), Boehringer Mannheim (Indianapolis, Ind.), and Genzyme (Cambridge, Mass.), or may prepared by well-known methods using chemical or enzymatic syntheses, or may be isolated from natural sources. Nucleotide-activated sugar analogs may also be prepared by the same methods. The donor is added in a 1.1 to 2 fold excess, or is regenerated in situ by known processes. See, for example: Ichikawa et al. *J. Amer. Chem. Soc.* 114:9283 (1992); Wong et al., *J. Org. Chem.* 57:4343 (1992); Ichikawa et al., *J. Amer. Chem. Soc.* 113:6300 (1991); and Wong et al., *J. Org. Chem.* 47:5416 (1982).

A common donor used in the enzymatic galactosylation is UDP-galactose. UDP-glucose may also be enzymatically epimerized in situ using the enzyme UDP-galactose 4-epimerase to form UDP-galactose (J. Thiem et al., *Angew. Chem.* 102, 78 (1990)). When the donor is used in stoichiometric amounts or in excess in the enzymatic glycosylation, it is necessary to decompose enzymatically the UDP liberated in the reaction using alkaline phosphatase, in order to prevent inhibition of the glycosyltransferase. See Unverzagt et al., *J. Amer. Chem. Soc.* 112:9308 (1990).

Other examples of nucleotide-activated sugars that may be used in the glycosylation include UDP-glucose, UDP-galactose, UDP-N-acetylglucosamine, UDP-N-acetylgalactosamine, UDP-glucuronic acid, CMP-neuraminic acid, GDP-fucose, GDP-mannose, dTDP-glucose and dUDP-galactose. Other UDP-activated sugars suitable for use in glycosylation reactions will be apparent to those of skill in the art. Processes known to the skilled worker for the preparation of nucleotide-activated sugars are described, for example in: Kittelmann et al., *Ann. N.Y. Acad. Sci.* 672:444 (Enzyme Engineering) (1992); Makino et al., *Tetrahedron Lett.* 34:2775 (1993); Martin et al., *Tetrahedron Lett.* 34:1765 (1993); European Patent Application 0 524 143 A1; Ikeda, *Carbohydrate Res.* 224:123 (1992); Kean *Glycobiology* 1:441 (1991); Ichikawa et al., *T. Org. Chem.* 57:2943 (1992); Adelhorst et al., *J. Org. Chem.* 57:2943 (1992); Adelhorst et al., *Carbohydrate Research* 242:69 (1993); Schmidt et al., *Liebigs Ann. Chem.* 1991:121; Stiller et al., *Liebigs Ann. Chem.* 1992:467; Heidlas et al., *J. org. Chem.* 57:146 (1992), Heidlas, *Acc. Chem. Res.* 25:307 (1992); Simon et al., *J. Org. Chem.* 55:1834 (1990); Wong et al. *J. Org. Chem.* 57:4343 (1992); and Pallanca et al., *J. Chem. Soc. Perkin Trans. I* 1993:3017.

The glycosylation reaction is carried out by adding about 0.01 to about 10 units of an appropriate glycosyltransferase are added to a solution of the acceptor the nucleotide-activated sugar dissolved in the aqueous buffer system. The glycosyltransferases are commercially available, for example from Sigma (St. Louis, Mo.), Boehringer Mannheim (Indianapolis, Ind.), and Genzyme (Cambridge, Mass.), or may be isolated from natural sources, or may be prepared by recombinant DNA technology. Examples of glycosyltransferases which may be used in the enzymatic glycosylation include:

β-1,4-galactosyltransferase [Barker et al., *J. Biol. Chem.* 247:7135 (1972) and Krezhorn et al., *Eur. J. Biochem.* 212:113 (1993)];

Gal-β-1-4-GlcNAcα-2-6-sialyltransferase [Paulson et al., *J. Biol. Chem.* 252:2363 (1977); Higa et al., *J. Biol. Chem.* 260:8838 (1985); and Weinstein et al., *J. Biol. Chem.* 257:13835 (1982)];

Gal-β-1-3-GalNAc α-2-3-sialyltransferase [Gillespie et al., *J. Biol. Chem.* 267:21004 (1992)];

Gal-β-1-3(4)-GlcNAc α-2-3-sialyltransferase [Weinstein et al., *J. Biol. Chem.* 257:13835 (1982) and Nemansky et al., *Glycoconjugate J.* 10:99 (1993)];

GalNAc α-2-6-sialyltransferase [Gros et al., *Biochemistry* 28:7386 (1989);

N-acetylglucosaminytransferases [Oehrlein et al., *Carbohydrate Res.* 244:149 (1993); Szumilo et al., *Biochemistry* 26:5498 (1987); Hindsgaul et al., *J. Biol. Chem.* 266:17858 (1991); and Look et al., *J. Org. Chem.* 58:4326 (1993)];

α-1-3-fucosyltransferase [Weston, *J. Biol. Chem.* 267:4152 (1992)];

α-1-2-fucosyltransferase [Beyer, *J. Bidl. Chem.* 255:5364 (1980)];

α-3-4-fucosyltransferase [Johnson, *Glycoconjugate J.* 9.241 (1992)];

α-1-2-mannosyltransferase [Wang, *J. Org. Chem.* 58:3985 (1993)]; and generally: Beyer et al., *Advances in Enzymology* 52:23 (1981) and WO 93/13198.

The enzymatic glycosylation is carried out at a temperature between about 10° C. to about 40° C., preferably at about 20° C. to about 37° C., particularly preferably at about 25° C. to 37° C., for 1 to 5 days. Once reaction is complete, as indicated by standard chromatography methods such as HPLC or TLC, the reaction is worked up by dialyzing against double-distilled water. The carbohydrate-containing polymer may subsequently be further purified by chromatography methods such as, for example, size exclusion chromatography.

The process according to the invention is particularly suitable for preparing carbohydrate-containing polymer with the following oligo- or disaccharide units:

Galβ1-4GlcNAc-;
Galβ1-3GlcNAc-,
SAα2-6Galβ1-4GlcNAc-;
SAα2-3Galβ1-4GlcNAc-;
SAα2-3Galβ1-3GlcNAc-;
Galβ1-4(Fucα1-3)GlcNAc-;
Galβ1-3(Fucα1-3)GlcNAc-;
SAα2-3Galβ1-3(Fucα1-4)GlcNAc-;
SAα2-3Galβ1-4(Fucα1-3)GlcNAc-;

sialyl-Lewis X, sialyl-Lewis A, VIM-2 and the following blood-group determinants Lewis A, B, X, Y and A type[1], A type[2], B type[1], B type[2] and H type[1], H type[2]. See, Lemieux, *Chem. Soc. Rev.*, 1978:423 and *Chem. Soc. Rev.* 1989:347.

Sialyl-Lewis X has the structure: NeuNAcα2-3Galβ1-4-(Fucα1-3)GlcNAc. Sialyl-Lewis A is: NeuNAcα2-3Galβ1-3(Fucα1-4)GlcNAc. VIM-2 is: NeuNAcα2-3Galβ1-4GlcNAcβ1-3Galβ1-4(Fucα1-3)GlcNAc. Detailed examples of the methods for the synthesis of mono- and oligosaccharide units are described below.

EXAMPLES

I. Reaction of the Polymer with the Carbohydrate Portion with the Bifunctional Spacer and with the Potentiator:

Example 1

1-(6-Aminohexyl)-2-deoxy-2-acetamido-β-D-glucopyranoside

2-Amino-2-deoxyglucose hydrochloride was converted by the method of Lemieux et al., (*ACS Symp.* Ser. 39, 90 (1976)) into 1,3,4,6-tetraacetyl-2-N-acetyl-2-deoxy-glucose by reaction with phthalic anhydride and subsequent reaction with acetic anhydride/pyridine. Treatment with tin tetrachloride/thiophenol by the method of Nicolaou et al., (*J. Amer. Chem. Soc.* 112:3695 (1990)) resulted in the corresponding 1-phenylthio derivative. The latter was reacted with 6-(N-benzyloxycarbonylamino)-hexanol by the method of Silwanis et al., (*J. Carbohydr. Chem.* 10:1067 (1991)). The acetyl and phthaloyl protective groups were cleaved with hydrazine hydrate by analogy to the method of Nicolaou et al., (*J. Amer. Chem. Soc.* 114:3127 (1992)). Prior to elimination of the benzyl protective groups ($H_2$/Pd(OH)$_2$, MeOH), the free amino group was selectively acetylated, in the presence of the free hydroxyl groups, with excess acetic anhydride. 1-(6-Aminohexyl)-2-deoxy-2-acetamido-β-D-glucopyranoside was obtained.

Example 2

Poly-D,L-succinimide-co-α,β-D,L-aspartamido-6-hexyl-2-deoxy-2-acetamido-β-D-glucopyranose
(Poly-D,L-succinimide-co-α,β-D,L-aspartamido-$C_6$-GlcNAc)

PSI (500 mg, MW 24,000) was dissolved in 2 ml of DMF, and 225 mg (0.71 mmol) of 1-(6-aminohexyl)-2-deoxy-2-acetamido-β-D-glucopyranoside (GlcNAc-$C_6$—$NH_2$) in 2.5 ml of DMF were added. The mixture was stirred at room temperature under $N_2$ for 5.5 hours. Precipitation of the polymer product with 40 ml of 1-butanol was followed by washing with methanol. After a second precipitation from DMF in 1-butanol, the product was again washed with methanol and subsequently dried under oil pump vacuum.

Yield: 490 mg.

Degree of substitution according to NMR: 12.5%.

Example 3

Poly-D,L-succinimide-co-α,β-D,L-aspartamido-6-hexyl-2-deoxy-2-acetamido-β-D-glucopyranose
(Poly-D,L-succinimide-co-α,β-D,L-aspartamido-$C_6$-GlcNAc)

In analogous fashion to Example 2, 320 mg of PSI (MW 24,000) was reacted with 300 mg of 1-(6-aminohexyl)-2-deoxy-2-acetamido-β-D-glucopyranoside (GlcNAc-$C_6$—$NH_2$) and worked up by precipitation twice from DMF with 1-butanol.

Yield: 383 mg. Degree of substitution according to NMR: 18.5%.

Example 4

Poly-D,L-succinimide-co-α,β-D,L-aspartamido-6-hexyl-2-deoxy-2-acetamido-β-D-gluco-pyranose
(Poly-D,L-succinimide-co-α,β-D,L-aspartamido-$C_6$-glcNAc)

In analogous fashion to Example 2, 480 mg of PSI (MW 9,600) were reacted with 210 mg of 1-(6-aminohexyl)-2-deoxy-2-acetamido-β-D-glucopyranoside (GlcNAc-$C_6$—$NH_2$) and worked up by precipitation twice from DMF with 1-butanol.

Yield: 485 mg. Degree of substitution according to NMR: 12.5%.

Example 5

Poly-D,L-succinimide-co-α,β-D,L-aspartamido-6-hexyl-2-deoxy-2-acetamido-β-D-gluco-pyranose
(Poly-D,L-succinimide-co-α,β-D,L-aspartamido-$C_6$glcNAc)

In analogous fashion to Example 2, 300 mg of PSI (MW 9,6000) were reacted with 280 mg of 1-(6-aminohexyl)-2-deoxy-2-acetamido-β-D-glucopyranoside (GlcNAc-$C_6$—$NH_2$) and worked up by precipitation twice from DMF with 1-butanol.

Yield: 331 mg. Degree of substitution according to NMR: 18%.

Example 6

Poly-a,g-(2-hydroxyethyl)-D,L-aspartamide-co-α,β-D,L-aspartamido-6-hexyl-2-deoxy-2-acetamido-o-D-glucopyranose (PHEA-co-aspartamido-$C_6$-GlcNAc)

PSI-co-aspartamido-$C_6$-GlcNAc from Example 2 (200 mg) was dissolved in 2 ml of DMF, and freshly distilled hydroxyethylamine (81 mg) was added. Stirring under $N_2$ at room temperature for 16 hours was followed by precipitation with 1-butanol. The polymer was washed with methanol, dissolved in $H_2O$ and freeze-dried.

Yield: 180 mg. Degree of substitution according to NMR: 87.5%; HEA, 12.5% GlcNAc-$C_6$—$NH_2$.

Example 7

Poly-α,β-(2-hydroxyethyl)-D,L-aspartamide-co-α,β-D,L-aspartamido-6-hexyl-2-deoxy-2-acetamido-β-D-glucopyranose (PHEA-co-aspartamido-$C_6$-GlcNAc)

PSI-co-aspartamido-$C_6$-GlcNAc from Example 3 (100 mg) was dissolved in 2 ml of DMF, and freshly distilled hydroxyethylamine (41 mg) was added. Stirring under $N_2$ at room temperature for 16 hours was followed by precipitation with 1-butanol. The polymer was washed with methanol, dissolved in $H_2O$ and freeze-dried.

Yield: 112 mg. Degree of substitution according to NMR: 83.5% HEA, 18.5% GlcNAc-$C_6$—$NH_2$.

Example 8

Poly-α,β-(2-hydroxyethyl)-D,L-aspartamide-co-α,β-D,L-aspartamido-6-hexyl-2-deoxy-2-acetamido-p-D-glucopyranose (PHEA-co-aspartamido-$C_6$-GalNAc)

PSI-co-aspartamido-$C_6$-GlcNAc from Example 4 (150 mg) was dissolved in 2 ml of DMF, and freshly distilled hydroxyethylamine (61 mg) was added. Stirring under $N_2$ at room temperature for 16 hours was followed by precipitation with 1-butanol. The polymer was washed with methanol, dissolved in $H_2O$ and freeze-dried.

Yield: 147 mg. Degree of substitution according to NMR: 87.5% HEA, 12.5% GlcNAc-$C_6$—$NH_2$.

Example 9

Poly-α,β-(2-hydroxyethyl)-D,L-aspartamide-co-α,β-D,L-aspartamido-6-hexyl-2-deoxy-2-acetamido-β-D-glucopyranose (PHE-co-aspartamido-$C_6$-GlcNAc)

PSI-co-aspartamido-$C_6$-GlcNAc from Example 5 (150 mg) was dissolved in 2 ml of DMF, and freshly distilled hydroxyethylamine (61 mg) was added. Stirring under $N_2$ at room temperature for 16 hours was followed by precipitation with 1-butanol. The polymer was washed with methanol, dissolved in $H_2O$ and freeze-dried.

Yield: 127 mg. Degree of substitution according to NMR: 82% HEA, 18% GlcNAc-$C_6$—$NH_2$.

Example 10

Poly-α,β-(2-hydroxyethyl)-D,L-aspartamide-co-α,β-D,L-aspartamido-6-hexyl-2-deoxy-2-acetamido-β-D-glucopyranose (PHEA-co-aspartamido-$C_6$-GlcNAc)

PSI-co-aspartamido-$C_6$-GlcNAc from Example 2 (170 mg) was dissolved in 2 ml of DMF, and freshly distilled hydroxyethylamine (43 mg) was added. stirring under $N_2$ at room temperature for 4 hours was followed by precipitation with 1-butanol. The polymer was washed with methanol, dissolved in $H_2O$ and freeze-dried.

Yield: 160 mg. Degree of substitution according to NMR: 61.5% HEA, 12.5% GlcNAc-$C_6$—$NH_2$.

Example 11

Poly-α,β-(2-hydroxyethyl)-D,L-aspartamide-co-α,β-D,L-aspartamido-6-hexyl-2-deoxy-2-acetamido-β-D-glucopyranose (PHEA-co-aspartamido-$C_6$-GlcNAc)

PSI-co-aspartamido-$C_6$-GlcNAc from Example 3 (120 mg) was dissolved in 2 ml of DMF, and freshly distilled hydroxyethylamine (30 mg) was added. Stirring under $N_2$ at room temperature for 4 hours was followed by precipitation with 1-butanol. The polymer was washed with methanol, dissolved in $H_2O$ and freeze-dried.

Yield: 126 mg. Degree of substitution according to NMR: 45.5% HEA, 18.5% GlcNAc-$C_6$—$NH_2$.

Example 12

Poly-α,β-(2-hydroxyethyl)-D,L-aspartamide-co-α,β-D,L-aspartamido-6-hexyl-2-deoxy-2-acetamido-β-D-glucopyranose (PHEA-co-aspartamido-$C_6$-GlcNAc)

PSI-co-aspartamido-$C_6$-GlcNAc from Example 4 (150 mg) was dissolved in 2 ml of DMF, and freshly distilled hydroxyethylamine (38 mg) was added. Stirring under $N_2$ at room temperature for 4 hours was followed by precipitation with 1-butanol. The polymer was washed with methanol, dissolved in $H_2O$ and freeze-dried.

Yield: 146 mg. Degree of substitution according to NMR: 56% HEA, 12.5% GlcNAc-$C_6$—$NH_2$.

Example 13

Poly-α,β-(2-hydroxyethyl)-D,L-aspartamide-co-α,β-D,L-aspartamido-6-hexyl-2-deoxy-2-acetamido-β-D-glucopyranose (PHEA-co-aspartamido-$C_6$-GlcNAc)

PSI-co-aspartamido-$C_6$-GlcNAc from Example 5 (150 mg) was dissolved in 2 ml of DMF, and freshly distilled hydroxyethylamine (38 mg) was added. Stirring under $N_2$ at room temperature for 4 hours was followed by precipitation with 1-butanol. The polymer was washed with methanol, dissolved in $H_2O$ and freeze-dried.

Yield: 143 mg. Degree of substitution according to NMR: 50% HEA, 12.5% GlcNAc-$C_6$—$NH_2$.

Example 14

Poly-D,L-succinimide-α,β-(5-carboxypentyl)-D,L-aspartamide 500 mg of PSI (MW 9,600) was dissolved in 2 ml of DMF, and 1.38 g of 6-aminohexanoic acid dissolved in 8 ml of formamide, and 1 ml of triethylamine were added. The mixture was stirred at 45° C. for 13 hours and subsequently precipitated with 1-butanol. The polymer was washed with methanol and then taken up in $H_2O$ and freeze-dried.

Yield: 350 mg. Degree of substitution according to NMR: 8% aminohexanoic acid.

Example 15

Poly-D,L-succinimide-α,β-(5-carboxypentyl)-D,L-aspartamide 500 mg of PSI (MW 24,000) was dissolved in 2 ml of DMF, and 690 mg of 6-aminohexanoic acid dissolved in 4 ml of formamide, and 1 ml of triethylamine were added. The mixture was stirred at room temperature for 3d and at 45° C. for 5 hours, and subsequently precipitated with 1-butanol. The polymer was washed with methanol and then taken up in $H_2O$ and freeze-dried.

Yield: 470 mg. Degree of substitution according to NMR: 12.5% aminohexanoic acid.

Example 16

Poly-D,L-succinimide-co-α,β-(5-carboxy-pentyl)-D,L-aspartamide-co-α,β-D,L-aspartamido-6-hexyl-2-deoxy-2-acetamido-β-D-gluco-pyranose (PCPA co-aspartamido-$C_6$-GlcNAc)

100 mg of PCPA from Example 14 was dissolved in 2 ml of $H_2O$, and 20 mg of 1-(6-aminohexyl)-2-deoxy-2- acetamido-β-D-glucopyranoside (GlcNAc-C$_6$—NH$_2$) was added. 20 mg portions of 1-ethyl-3-(3-dimethylaminopropyl) carbodiimide hydrochloride (EDC) were added 4 times over the course of 36 hours. The product was obtained by dialysis and freeze-drying.

Yield: 112 mg. Degree of substitution according to NMR: 8% GlcNAc-O(CH$_2$)$_6$NH$_2$.

Example 17

Poly-D,L-succinimide-co-α,β-(5-carboxy-pentyl)-D,L-aspartamide-co-α,β-D,L-aspartamido-6-hexyl-2-deoxy-2-acetamido-β-D-gluco-pyranose (PCPAC-co-aspartamido-C$_6$-GlcNAc)

100 mg of PCPA from Example 15 was dissolved in 2 ml of H$_2$O, and 20 mg of 1-(6-aminohexyl)-2-deoxy-2-acetamido-β-D-glucopyranoside (GlcNAc-C$_6$—NH$_2$) was added. 20 mg portions of 1-ethyl-3-(3-dimethylaminopropyl) carbodiimide hydrochloride (EDC) were added 4 times over the course of 36 hours. The product was obtained after dialysis and freeze-drying.

Yield: 137 mg. Degree of substitution according to NMR: 12.5% GlcNAc-O(CH$_2$)$_6$NH$_2$.

II. Enzymatic Galactosylation Reactions:

Example 18

Enzymatic Galactosylation of Poly-D,L-succinimide-co-α,β-aspartamido-C$_6$-GlcNAc 50 mg of the polymer from Example 2 was dissolved in 10 ml of 0.05 M HEPES buffer pH 7.5, and 2 mg of MnCl$_2$ and 55 mg of UDP-glucose plus 1 mg of lactalbumin were added. After addition of 2 U of UDP-galactose 4-epimerase, 2 U of galactosyltransferase and 40 U of alkaline phosphatase (from calf intestine), the mixture was incubated at 25° C. for 8 days. Dialysis against water was followed by freeze-drying and subsequent chromatography on Sephadex G 10. The product was obtained after freeze-drying.

Yield: 74 mg. Degree of LacNAc substitution according to NMR: 12.5%.

Example 19

Enzymatic Galactosylation of Poly-D,L-succinimide-co-α,β-aspartamido-C$_6$-GlcNAc 50 mg of the polymer from Example 3 was dissolved in 10 ml of 0.05 M HEPES buffer pH 7.5, and 2 mg of MnCl$_2$ and 55 mg of UDP-glucose plus 1 mg of lactalbumin were added. After addition of 2 U of UDP-galactose 4-epimerase, 2 U of galactosyltransferase and 40 U of alkaline phosphatase (from calf intestine) the mixture was incubated at 25° C. for 8 days. Dialysis against water was followed by freeze-drying and subsequent chromatography on Sephadex G 10. The product was obtained after freeze-drying.

Yield: 76 mg. Degree of LacNAc substitution according to NMR: 18.5%.

Example 20

Enzymatic Galactosylation of Poly-D,L-succinimide-co-α,β-aspartamido-C$_6$-GlcNAc 50 mg of the polymer from Example 4 was dissolved in 10 ml of 0.05 M HEPES buffer pH 7.5, and 2 mg of MnCl$_2$ and 55 mg of UDP-glucose plus 1 mg of lactalbumin were added. After addition of 2 U of UDP-galactose 4-epimerase, 2 U of galactosyltransferase and 40 U of alkaline phosphatase (from calf intestine) the mixture was incubated at 25° C. for 8 days. Dialysis against water was followed by freeze-drying and subsequent chromatography on Sephadex G 10. The product was obtained after freeze-drying.

Yield: 77 mg. Degree of LacNAc substitution according to NMR: 12.5%.

Example 21

Enzymatic Galactosylation of Poly-D,L-succinimide-co-α,β-aspartamido-C$_6$-GlcNAc 50 mg of the polymer from Example 5 was dissolved in 10 ml of 0.05 M HEPES buffer pH 7.5, and 2 mg of MnCl$_2$ and 55 mg of UDP-glucose plus 1 mg of lactalbumin were added. After addition of 2 U of UDP-galactose 4-epimerase, 2 U of galactosyltransferase and 40 U of alkaline phosphatase (from calf intestine), the mixture was incubated at 25° C. for 8 days. Dialysis against water was followed by freeze-drying and subsequent chromatography on Sephadex G 10. The product was obtained after freeze-drying.

Yield: 78 mg. Degree of LacNAc substitution according to NMR: 18%.

Example 22

Enzymatic Galactosylation of Poly-α,β-(2-hydroxyethyl)-D,L-aspartamide-co-a,b-D,L-aspartamido-6-hexyl-2-deoxy-2-acetamido-β-D-glucopyranose (PHEA-co-aspartamido-C$_6$-GlcNAc)

50 mg of the polymer from Example 6 was dissolved in 10 ml of 0.05 M HEPES buffer pH 7.5, and 2 mg of MnCl$_2$ and 40 mg of UDP-glucose plus 1 mg of lactalbumin were added. After addition of 2 U of UDP-galactose 4-epimerase, 2 U of galactosyltransferase and 40 U of alkaline phosphatase (from calf intestine), the mixture was incubated at 25° C. for 7 days. Dialysis against water was followed by freeze-drying and subsequent chromatography on Sephadex G 10. The product was obtained after freeze-drying.

Yield: 70.6 mg. Degree of LacNAc substitution according to NMR: 12.5%.

Example 23

Enzymatic Galactosylation of Poly-α,β-(2-hydroxyethyl)-D,L-aspartamide-co-α,β-D,L-aspartamido-6-hexyl-2-deoxy-2-acetamido-3-D-glucopyranose (PHEA-co-aspartamido-C$_6$-GlcNAc)

50 mg of the polymer from Example 7 was dissolved in 10 ml of 0.05 M HEPES buffer pH 7.5, and 2 mg of MnCl$_2$ and 40 mg of UDP-glucose plus 1 mg of lactalbumin were added. After addition of 2 U of UDP-galactose 4-epimerase, 2 U of galactosyltransferase and 40 U of alkaline phosphatase (from calf intestine), the mixture was incubated at 25° C. for 7 days. Dialysis against water was followed by freeze-drying and subsequent chromatography on Sephadex G 10. The product was obtained after freeze-drying.

Yield: 69 mg. Degree of LacNAc substitution according to NMR: 18.5%.

Example 24

Enzymatic Galactosylation of Poly-α,β-(2-hydroxyethyl-D,L-aspartamide-co-α,β-D,L-aspartamido-6-hexyl-2-deoxy-2-acetamido-β-D-glucopyranose (PHEA-co-aspartamido-C$_6$-GlcNAc)

50 mg of the polymer from Example 8 was dissolved in 10 ml of 0.05 M HEPES buffer pH 7.5, and 2 mg of MnCl$_2$ and 40 mg of UDP-glucose plus 1 mg of lactalbumin were added. After addition of 2 U of UDP-galactose 4-epimerase, 2 U of galactosyltransferase and 40 U of alkaline phosphatase (from calf intestine), the mixture was incubated at 25° C. for 7 days. Dialysis against water was followed by freeze-drying and subsequent chromatography on Sephadex G 10. The product was obtained after freeze-drying.

Yield: 55 mg. Degree of LacNAc substitution according to NMR: 12.5%.

Example 25

Enzymatic Galactosylation of Poly-α,β-(2-hydroxyethyl)-D,L-aspartamide-co-α,β-D,L-aspartamido-6-hexyl-2-deoxy-2-acetamido-β-D-glucopyranose (PHEA-co-aspartamido-$C_6$-GlcNAc)

50 mg of the polymer from Example 9 was dissolved in 10 ml of 0.05 M HEPES buffer pH 7.5, and 2 mg of $MnCl_2$ and 40 mg of UDP-glucose plus 1 mg of lactalbumin were added. After addition of 2 U of UDP-galactose 4-epimerase, 2 U of galactosyltransferase and 40 U of alkaline phosphatase (from calf intestine), the mixture was incubated at 25° C. for 7 days. Dialysis against water was followed by freeze-drying and subsequent chromatography on Sephadex G 10. The product was obtained after freeze-drying.

Yield: 55 mg. Degree of LacNAc substitution according to NMR: 18%.

Example 26

Enzymatic Galactosylation of Poly-α,β-(2-hydroxyethyl)-D,L-aspartamide-co-α,β-D,L-aspartamido-6-hexyl-2-deoxy-2-acetamido-β-D-glucopyranose (PHEA-co-aspartamido-$C_5$-GlcNAc)

50 mg of the polymer from Example 10 was dissolved in 10 ml of 0.05 M HEPES buffer pH 7.5, and 2 mg of $MnCl_2$ and 40 mg of UDP-glucose plus 1 mg of lactalbumin were added. After addition of 2 U of UDP-galactose 4-epimerase, 2 U of galactosyltransferase and 40 U of. alkaline phosphatase (from calf intestine) the mixture was incubated at 25° C. for 7 days. Dialysis against water was followed by freeze-drying and subsequent chromatography on Sephadex G 10. The product was obtained after freeze-drying.

Yield: 54 mg. Degree of LacNAc substitution according to NMR: 12.5%.

Example 27

Enzymatic Galactosylation of Poly-α,β-(2-hydroxyethyl)-D,L-aspartamide-co-α,β-D,L-aspartamido-6-hexyl-2-deoxy-2-acetamido-β-D-glucopyranose (PHEA-co-aspartamido-$C_6$-GlcNAc)

50 mg of the polymer from Example 11 was dissolved in 10 ml of 0.05 M HEPES buffer pH 7.5, and 2 mg of $MnCl$, and 40 mg of UDP-glucose plus 1 mg of lactalbumin were added. After addition of 2 U of UDP-galactose 4-epimerase, 2 U of galactosyltransferase and 40 U of alkaline phosphatase (from calf intestine), the mixture was incubated at 25° C. for 7 days. Dialysis against water was followed by freeze-drying and subsequent chromatography on Sephadex G 10. The product was obtained after freeze-drying again.

Yield: 71 mg. Degree of LacNAc substitution according to NMR: 18.5%.

Example 28

Enzymatic Galactosylation of poly-α,β-(2-hydroxyethyl)-D,L-aspartamide-co-α,β-D,L-aspartamido-6-hexyl-2-deoxy-2-acetamido-β-D-glucopyranose (PHEA-co-aspartamido-$C_6$-GlcNAc)

50 mg of the polymer from Example 12 was dissolved in 10 ml of 0.05 M HEPES buffer pH 7.5, and 2 mg of $MnCl_2$ and 40 mg of UDP-glucose plus 1 mg of lactalbumin were added. After addition of 2 U of UDP-galactose 4-epimerase, 2 U of galactosyltransferase and 40 U of alkaline phosphatase (from calf intestine), the mixture was incubated at 25° C. for 7 days. Dialysis against water was followed by freeze-drying and subsequent chromatography on Sephadex G 10. The product was obtained after freeze-drying.

Yield: 66 mg. Degree of LacNAc substitution according to NMR: 12.5%.

Example 29

Enzymatic Galactosylation of Poly-α,β-(2-hydroxyethyl-D,L-aspartamide-co-α,β-D,L-aspartamido-6-hexyl-2-deoxy-2-acetamido-β-D-glucopyranose (PHEA-co-aspartamido-$C_6$-GlcNAc)

50 mg of the polymer from Example 13 was dissolved in 10 ml of 0.05 M HEPES buffer pH 7.5, and 2 mg of $MnCl_2$ and 40 mg of UDP-glucose plus 1 mg of lactalbumin were added. After addition of 2 U of UDP-galactose 4-epimerase, 2 U of galactosyltransferase and 40 U of alkaline phosphatase (from calf intestine), the mixture was incubated at 25° C. for 7 days. Dialysis against water was followed by freeze-drying and subsequent chromatography on Sephadex G 10. The product was obtained after freeze-drying.

Yield: 64 mg. Degree of LacNAc substitution according to NMR: 18%.

III. Enzymatic Sialylation

Example 30

Enzymatic Sialylation of Poly-D,L-succinimide-co-α,β-aspartamido-$C_6$-LacNAc 35 mg of the polymer from Example 18 was dissolved in 2 ml of 0.05 M sodium cacodylate buffer pH 7.8, and 1.5 mg of bovine serum albumin, 2 mg of $MnCl_2$ and 5 mg of CMP-neuraminic acid were added. Addition of 20 mU of 2-6-sialyltransferase and 20 U of alkaline phosphatase was followed by incubation at 25° C. for 8 days. Dialysis against water was followed by freeze-drying and subsequent chromatography on Biogel P2. The product was obtained after freeze-drying.

Yield: 36.6 mg. Degree of 2,6-sialyl-LacNAc substitution: 12.5% (0.65 μmol/mg polymer).

Example 31

Enzymatic Sialylation of poly-D,L-succinimide-co-α,β-aspartamido-$C_6$-LacNAc 30 mg of the polymer from Example 19 was dissolved in 2 ml of 0.05 M sodium cacodylate buffer pH 7.8, and 1.5 mg of bovine serum albumin, 2 mg of $MnCl_2$ and 5 mg of CMP-neuraminic acid were added. Addition of 20 mU of 2-6-sialyltransferase and 20 U of alkaline phosphatase was followed by incubation at 25° C. for 8 days. Dialysis against water was followed by freeze-drying and subsequent chromatography on Biogel P2. The product was obtained after freeze-drying.

Yield: 32 mg. Degree of 2,6-sialyl-LacNAc substitution: 18.5% (0.77 μmol/mg polymer).

Example 32

Enzymatic Sialylation of Poly-D,L-succinimide-co-α,β-aspartamido-$C_6$-LacNAc 30 mg of the polymer from Example 20 was dissolved in 2 ml of 0.05 M sodium cacodylate buffer pH 7.8, and 1.5 mg of bovine serum albumin, 2 mg of $MnCl_2$ and 5 mg of CMP-neuraminic acid were added. Addition of 20 mU of 2-6-sialyltransferase and 20 U of alkaline phosphatase was followed by incubation at 25° C. for 8 days. Dialysis against water was followed by freeze-drying and subsequent chromatography on Biogel P2. The product was obtained after freeze-drying.

Yield: 21 mg. Degree of 2,6-sialyl-LacNAc substitution: 12.5% (0.65 µmol/mg polymer).

Example 33

Enzymatic Sialylation of Poly-D,L-succinimide-co-α,β-aspartamido-$C_6$-LacNAc 35 mg of the polymer from Example 21 was dissolved in 2 ml of 0.05 M sodium cacodylate buffer pH 7.8, and 1.5 mg of bovine serum albumin, 2 mg of $MnCl_2$ and 5 mg of CMP-neuraminic acid were added. Addition of 20 mU of 2-6-sialyltransferase and 20 U of alkaline phosphatase was followed by incubation at 25° C. for 8 days. Dialysis against water was followed by freeze-drying and subsequent chromatography on Biogel P2. The product was obtained after freeze-drying.

Yield: 38 mg. Degree of 2,6-sialyl-LacNAc substitution: 18% (0.76 µmol/mg polymer).

Example 34

Enzymatic Sialylation of Poly-α,β(2-hydroxyethyl)-D,L-aspartamide-co-α,β-D,L-aspartamido-6-hexyl-O-(β-D-galactopyranosyl)-(1-4)-2-deoxy-2-acetamido-β-D-glucopyranose (PHEA-co-aspartamido-$C_6$-LacNAc)

35 mg of the polymer from Example 22 was dissolved in 2 ml of 0.05 M sodium cacodylate buffer pH 7.8, and 1.5 mg of bovine serum albumin, 2 mg of $MnCl_2$ and 5 mg of CMP-neuraminic acid were added. Addition of 20 mU of 2-6-sialyltransferase and 20 U of alkaline phosphatase was followed by incubation at 25° C. for 8 days. Dialysis against water was followed by freeze-drying and subsequent chromatography on Biogel P2. The product was obtained after freeze-drying.

Yield: 29 mg. Degree of 2,6-sialyl-LacNAc substitution: 12.5% (0.51 µmol/mg polymer).

Example 35

Enzymatic Sialylation of Poly-α,β-(2-hydroxyethyl)-D,L-aspartamide-co-α,β-D,L-aspartamido-6-hexyl-O-(β-D-galactopyranosyl)-(1-4)-2-deoxy-2-acetamido-β-D-glucopyranose (PHEA-co-aspartamido-$C_6$-LacNAc)

35 mg of the polymer from Example 23 was dissolved in 2 ml of 0.05 M sodium cacodylate buffer pH 7.8, and 1.5 mg of bovine serum albumin, 2 mg of $MnCl_2$ and 5 mg of CMP-neuraminic acid were added. Addition of 20 mU of 2-6-sialyltransferase and 20 U of alkaline phosphatase was followed by incubation at 25° C. for 8 days. Dialysis against water was followed by freeze-drying and subsequent chromatography on Biogel P2. The product was obtained after freeze-drying.

Yield: 29 mg. Degree of 2,6-sialyl-LacNAc substitution: 18.5% (0.64 µmol/mg polymer).

Example 36

Enzymatic Sialylation of Poly-α,β-(2-hydroxyethyl)-D,L-aspartamide-co-α,β-D,L-aspartamido-6-hexyl-O-(β-D-galactolyranosyl)-(1-4)-2-deoxy-2-acetamido-β-D-glucopyranose (PHEA-co-aspartamido-$C_6$-LacNAc)

35 mg of the polymer from Example 24 was dissolved in 2 ml of 0.05 M sodium cacodylate buffer pH 7.8, and 1.5 mg of bovine serum albumin, 2 mg of $MnCl_2$ and 5 mg of CMP-neuraminic acid were added. Addition of 20 mU of 2-6-sialyltransferase and 20 U of alkaline phosphatase was followed by incubation at 25° C. for 8 days. Dialysis against water was followed by freeze-drying and subsequent chromatography on Biogel P2. The product was obtained after freeze-drying.

Yield: 34 mg. Degree of 2,6-sialyl-LacNAc substitution: 12.5% (0.51 µmol/mg polymer).

Example 37

Enzymatic Sialylation of Poly-α,β-(2-hydroxyethyl)-D,L-aspartamide-co-α,β-D,L-aspartamido-6-hexyl-O-(β-D-galactopyranosyl)-(1-4)-2-deoxy-2-acetamido-β-D-glucopyranose (PHEA-co-aspartamido-$C_6$-LacNAc)

25 mg of the polymer from Example 25 was dissolved in 2 ml of 0.05 M sodium cacodylate buffer pH 7.8, and 1.5 mg of bovine serum albumin, 2 mg of $MnCl_2$ and 5 mg of CMP-neuraminic acid were added. Addition of 20 mU of 2-6-Sialyltransferase and 20 U of alkaline phosphatase was followed by incubation at 25° C. for 8 days. Dialysis against water was followed by freeze-drying and subsequent chromatography on Biogel P2. The product was obtained remains after freeze-drying.

Yield: 25 mg. Degree of 2,6-Sialyl-LacNAc substitution: 18% (0.63 µmol/mg polymer).

Example 38

Enzymatic Sialylation of Poly-α,β-(2-hydroxyethyl)-D,L-aspartamide-co-α,β-D,L-aspartamido-6-hexyl-O-(β-D-galactopyranosyl)-(1-4)-2-deoxy-2-acetamido-β-D-glucopyranose (PHEA-co-aspartamido-$C_6$-LacNAc)

35 mg of the polymer from Example 26 was dissolved in 2 ml of 0.05 M sodium cacodylate buffer pH 7.8, and 1.5 mg of bovine serum albumin, 2 mg of $MnCl_2$ and 5 mg of CMP-neuraminic acid were added. Addition of 20 mU of 2-6-sialyltransferase and 20 U of alkaline phosphatase was followed by incubation at 25° C. for 8 days. Dialysis against water was followed by freeze-drying and subsequent chromatography on Biogel P2. The product was obtained after freeze-drying.

Yield: 28 mg. Degree of 2,6-sialyl-LacNAc substitution: 12.5% (0.54 µmol/mg polymer).

Example 39

Enzymatic Sialylation of Poly-α,β-(2-hydroxyethyl)-D,L-aspartamide-co-α,β-D,L-aspartamido-6-hexyl-O-(β-D-galactopyranosyl)-(1-4)-2-deoxy-2-acetamido-β-D-glucopyranose (PHEA-co-aspartamido-$C_6$-LacNAc)

35 mg of the polymer from Example 27 was dissolved in 2 ml of 0.05 M sodium cacodylate buffer pH 7.8, and 1.5 mg of bovine serum albumin, 2 mg of $MnCl_2$ and 5 mg of CMP-neuraminic acid were added. Addition of 20 mU of 2-6-sialyltransferase and 20 U of alkaline phosphatase was followed by incubation at 25° C. for 8 days. Dialysis against water was followed by freeze-drying and subsequent chromatography on Biogel P2. The product was obtained after freeze-drying.

Yield: 33 mg. Degree of 2,6-sialyl-LacNAc substitution: 18.5% (0.69 µmol/mg polymer).

Example 40

Enzymatic Sialylation of Poly-α,β-(2-hydroxyethyl)-D,L-aspartamide-co-α,β-D,L-aspartamido-6-hexyl-O-(β-D-galactopyranosyl)-(1-4)-2-deoxy-2-acetamido-β-D-glucopyranose (PHEA-co-aspartamido-$C_6$-LacNAc)

35 mg of the polymer from Example 28 was dissolved in 2 ml of 0.05 M sodium cacodylate buffer pH 7.8, and 1.5 mg of bovine serum albumin, 2 mg of $MnCl_2$ and 5 mg of CMP-neuraminic acid were added. Addition of 20 mU of 2-6-sialyltransferase and 20 U of alkaline phosphatase was followed by incubation at 25° C. for 8 days. Dialysis against water was followed by freeze-drying and subsequent chromatography on Biogel P2. The product was obtained after freeze-drying.

Yield: 31 mg. Degree of 2,6-sialyl-LacNAc substitution: 12.5% (0.55 μmol/mg polymer).

Example 41

Enzymatic Sialylation of Poly-α,β-(2-hydroxyethyl)-D,L-aspartamide-co-α,β-B-D,L-aspartamido-6-hexyl-O-(β-D-galactopyranosyl)-(1-4)-2-deoxy-2-acetamido-β-D-glucopyranose (PHEA-co-aspartamido-$C_6$-LacNAc)

35 mg of the polymer from Example 29 was dissolved in 2 ml of 0.05 M sodium cacodylate buffer pH 7.8, and 1.5 mg of bovine serum albumin, 2 mg of $MnCl_2$ and 5 mg of CMP-neuraminic acid were added. Addition of 20 mU of 2-6-sialyltransferase and 20 U of alkaline phosphatase was followed by incubation at 25° C. for 8 days. Dialysis against water was followed by freeze-drying. and subsequent chromatography on Biogel P2. The product was obtained after freeze-drying.

Yield: 15 mg. Degree of 2,6-sialyl-LacNAc substitution: 18% (0.68 μmol/mg polymer).

Example 42

A: Primary Assays for Investigating the Effect of Polymeric Carbohydrate Receptor Blockers on Cell Adhesion to Recombinant Soluble Selectin Fusion Proteins This assay was used to detect the effect of polymer-bound carbohydrate units on cell adhesion of promyelocytic cells via selectins. The assay used to test the activity of polymer-bound carbohydrate units on the interaction between E- and P-selectins (also known as ELAM-1 and GMP-140, respectively) and their ligands is specific for only one of these interactions in each case. The natural form of the ligands appear on the surface of promyelocytic HL60 cells. Since HL60 cells have multiple ligands and adhesion molecules of widely differing specificity, the required specificity of the assay can be provided only via the binding partner i.e. the receptor. Accordingly, genetically engineered soluble fusion proteins formed between the extracytoplasmic domain of E- or P-selectin together with the constant region of a human immunoglobulin of subclass IgG1 were used.

A1. Preparation of L-selectin-IgG1

The genetic construct "ELAM-Rg" described by Walz et al., Science 250, 1132–1135 (1990) was used to prepare soluble L-selectin-IgG1 fusion protein. Briefly, plasmid DNA was transfected into COS-7 cells (ATCC) using DEAE-dextran by standard methods. See Ausubel et al., Current Protocols in Molecular Biology, John Wiley, New York, (1990). Seven days after transfection, the culture supernatant was centrifuged to remove cells and cell fragments and adjusted to 25 mM Hepes, pH 7.0, 0.3 mM PMSF, and 0.02% sodium azide, and stored at +4° C.

A2. Preparation of P-selectin-IgG1

The genetic construct "CD62Rg" described by Aruffo et al., Cell, 67:35 (1991) was used to prepare the soluble P-selectin-IgG1 fusion protein. The subsequent procedure corresponds to the preparation of L-selectin-IgG1 described above at Section A1.

A3. Preparation of CD4-IgG1

The genetic construct "CD4:IgG1 hinge" described by Zettlemeissl et al., DNA and Cell Biology 9:347 (1990), was used to prepare the soluble CD4-IgG1 fusion protein. The subsequent procedure corresponds to the preparation of L-selectin-IgG1 described above at Section A1.

A4. Procedure for the HL60 Cell Adhesion Assay for Recombinant Soluble Adhesion Molecules 1. 96-well microliter assay plates (Nunc Maxisorb) were incubated with 100 μl of a goat anti-human IgG antibody (Sigma) diluted (1+100) in 50 mM Tris pH 9.5 at room temperature for 2 h. Removal of the antibody solution was followed by one wash with PBS.

2. 150 μl of the blocking buffer was left in the wells at room temperature for 1 h. The composition of the blocking buffer was: 0.1% gelatin, 1% BSA, 5% calf serum, 0.2 mM PMSF, 0.02% sodium azide. Removal of the blocking buffer was followed by one wash with PBS.

3. 100 μl of cell culture supernatant from appropriately transfected and expressing COS cells were pipetted into each of the wells, followed by incubation at room temperature for 2 h. Removal of the cell culture supernatant was followed by one wash with PBS.

4. 20 μl of binding buffer was placed in the wells. The binding buffer had the composition: 50 mM Hepes, pH 7.5; 100 mM NaCl; 1 mg/ml BSA; 2 mM $MgCl_2$, 1 mM $CaCl_2$; 3 mM $MnCl_2$; 0.02% sodium azide; 0.2 mM PMSF. 5 μl of the test substance were added by pipette, mixed by agitating the plate and incubated at room temperature for 10 min.

5. 50 ml of an HL60 cell culture with 200,000 cells/ml were centrifuged at 350 g for 4 min. The pellet was resuspended in 10 ml of RPMI 1640 and the cells were again centrifuged. For labeling of the cells, 50 μg of BCECF-AM (Molecular Probes) were dissolved in 5 μl of anhydrous DMSO; subsequently 1.5 ml of RPMI 1640 was added to the BCECF-AM/DMSO solution. The cells were resuspended in this solution and incubated at 37° C. for 30 min. After centrifugation at 350 g for 2 minutes, the labeled cell pellet was resuspended in 11 ml of binding buffer, and the resuspended cells distributed in 100 μl aliquots in the wells of the microtiter plate. The plate was left to stand at room temperature for 10 min in order to allow the cells to sediment to the bottom of the test plate and to adhere to the coated plastic.

6. To stop the assay, the microtiter plate was completely immersed at an angle of 45° in the stop buffer (25 mM Tris, pH 7.5; 125 mM NaCl; 0.1% BSA; 2 mM $mgCl_2$; 1 mM $CaCl_2$; 3 mM $MnCl_2$; 0.02% sodium azide). The stop buffer was removed from the wells by inversion, and the procedure was repeated twice more.

7. The BCECF-AM-labeled cells which were firmly adherent in the wells were measured in a cytofluorimeter (Millipore) with a sensitivity setting of 4, an excitation wavelength of 485/22 nm and an emission wavelength of 530/25 nm.

$IC_{50}$ of HL60 cell adhesion to E-selectin-IgG;
Compound from Ex. 30: 60 μM
 31: 60 μM
 32: 100 μM 33: 60 μM
34: 150 μM
Comparative value: $IC_{50}$ of HL60 cell adhesion to E-selectin-IgG: Sialyl-Le$^x$—O(CH$_2$)$_6$NH$_2$: 1 mM (c.f., EPA 93 119 098.7)

B. Secondary Assay to Investigate the Effect of Polymeric Carbohydrate Receptor Blockers on Cell Adhesion to Stimulated Human Endothelial Cells The ability of carbohydrate-containing polymer to block cell adhesion to recombinant soluble fusion proteins can be measured in a highly specific assay based on the interaction of one type of adhesion molecules with the corresponding ligands. In order to simulate the in vivo situation of cell-cell interactions, the assay used the adhesion of HL60 cells to stimulated human umbilical endothelial cells (HUVECs).

B1. Obtaining the Human Umbilical Endothelial Cells (HUVEC)

Umbilical cords were stored after delivery in PBS containing 100,000 IU/L penicillin, 100 mg/L streptomycin, 50 mg/L gentamicin and 50,000 IU/L mycostatin at +4° C. until further processed. The longest undamaged pieces were cut out of the umbilical cord with a scalpel and placed on fresh aluminum foil. One end of the umbilical cord was closed with a clip. At the other end, a suitable tube was inserted into the umbilical vein and fixed by ligating the end of the umbilical cord.

The vein was filled through the tube with collagenase solution (50 mg collagenase/100 ml 25 mM Hepes, pH 7.0) and incubated at 37° C. for 15 min. To increase the cell yield, the umbilical cord was gently massaged after the incubation in order to detach still-adherent endothelial cells.

The cell suspension was subsequently allowed to run out of the vein into a culture tube containing cell culture medium and 10% fetal calf serum. The vein was washed with PBS to obtain the remaining cells. The cell suspension was then centrifuged at 500 g for 5 min; the cell pellet was subsequently resuspended in 4 ml of culture medium and the cells were plated out. After 3–4 days confluent growth of the cells occurred and they could be passaged normally.

To check the purity of the endothelial cell culture, the culture was stained with an immunofluorescent labeled antibody against factor VIII. Positive reaction was shown only by endothelial cells but not by contaminating fibroblasts.

B2. Assay Protocol 20,000 endothelial cells per well were plated out in a 96-well microtiter plate and incubated. at 37° C. for 24 h. The endothelial cells for this purpose were passaged fewer than 5–6 times. Four hours before the assay the endothelial cells were stimulated by addition of Il-1 (final concentration: 15 U/ml). After removal of the culture medium, the cells were washed once with RPMI medium without serum. Removal and renewed pipetting of 20 μl of RPMI medium were followed by addition of test compounds.

C. Secondary Assay to Investigate the Effect of Carbohydrate-containing Polymer on Cell Adhesion to Frozen Sections of Lymphatic Tissue It is possible to investigate in vitro the extent to which leukocytes bind to endothelial cells on frozen sections of lymphatic tissue. These cell-cell interactions are based on the interaction between adhesion molecules on the surface of the endothelial cells in the frozen section and the corresponding ligands on the surface of leukocytes. It is possible to use HL60 cells, whose surface ligands are well described in the scientific literature, as substitutes for primary leukocytes. The adhesion of HL60 cells to lymph node frozen sections can be measured using the number of bound HL60 cells.

1. Axillary, cervical or mesenteric lymph nodes were dissected out of freshly sacrificed rats and rapidly frozen in liquid nitrogen.

2. 10 μm-thick cryostat sections were prepared from the frozen lymph nodes, transferred to circular cover glasses (diameter 18 mm) and dried at room temperature for 2 h.

3. 20 μl of binding buffer was pipetted onto the sections. The test substances were added and incubated at room temperature for 10 min. HL60 cells were labeled as described above at Section A4. 200,000 labeled HL60 cells in 100 μl of binding buffer were added to each cover glass and left to stand for 10 min. This allows the sedimenting cells to adhere to the endothelial cells.

4. The cover glasses were immersed at an angle of 45° in stop buffer in order to rinse off the non-adherent cells. The cover glasses were subsequently fixed in 4% formaldehyde in PBS at room temperature for 10 min.

5. Cross sections of lymphatic blood vessels were recorded by photography under an immunofluorescence microscope (FITC excitation). The adherent HL60 cells were clearly distinct from the unstained background. Following counting, the results were expressed as bound HL60 cells per unit area of endothelium.

D. Tertiary Assay to Investigate the Effect of Carbohydrate-containing Polymer on Leukocyte Adhesion in Rats in Vivo The method detailed hereinafter establishes the in vivo activity of substances that inhibit the adhesion of leukocytes to the vessel intima.

It is known that some circulating white blood cells tend to adhere to the intima of the blood vessels. This tendency is significantly enhanced in inflammatory processes. Leukocytes normally impinge continually on blood vessel walls, but this collision is elastic and the cells rebound to a certain extent. and return to the circulation. In inflammatory processes, biochemical changes in the leukocytes and in the endothelial cells lining the blood vessels lead to increases in the adhesive properties of both types of cell. This adhesiveness is initially marked by the tendency of leukocytes after collision with the endothelium to roll on the endothelial cells. This rolling induces further biochemical reactions in both binding partners, leading to enhanced cell adhesion. This slows down the rolling of the leukocytes until they adhere firmly to the endothelium. The leukocytes then migrate out of the blood vessel into the surrounding tissue. This effect can be induced with leukocyte-stimulating factors such as FMLP (f-Met-Leu-Phe), LPS (lipopolysaccharides) or TNF (tumor necrosis factor). Microscopic recording of these processes is possible on dissected mesenteric tissue, for example from rats. The ability of substances injected into the bloodstream to influence induced leukocyte adhesion can thus be determined.

Rats were anesthetized and the abdominal cavity was opened. A section of the small intestine was pulled out and continuously kept moist on a heatable microscope stage. For microscopic inspection, a region of mesenteric tissue was covered with liquid paraffin. For the control, all the adherent—nonstimulated—leukocytes in this region were counted every 5 min for a period of 30 min. In parallel with this, the blood pressure, body temperature and flow rate of the blood were recorded. The test substance was administered by continuous venous infusion throughout the test. After application of leukocyte stimulants, which were added dropwise to the mesenteric tissue, the adherent leukocytes were counted every 5 min for a period of 90 min.

The investigation was carried out on test groups each composed of three animals. The first animal received only the vehicle in order to determine the spontaneous adhesion.

The second animal received the leukocyte stimulator only, to determine the pathogenic control. The third animal received leukocyte stimulant and test substance.

The number of adherent "leukocytes in the pathogenic control was set at 100%. The percentage change in the leukocyte adhesion on administration of test substance compared with the pathogenic control indicated the activity of a test substance.

EXPRESS INCORPORATION BY REFERENCE

Each of the publications cited in this specification is hereby expressly incorporated herein, in its entirety, by reference. Additionally, the complete specifications of application Ser. No. 08/165,805, now allowed, PCT application no. PCT/EP95/02285, German Patent Applications P 44 20 943.6, filed Jun. 16, 1994, P 42 41 829.1, filed Dec. 11, 1992, and P 43 26 777.7, filed Aug. 10, 1993, are expressly incorporated herein by reference.

What is claimed is:

1. A process for preparing a carbohydrate-containing polymer that is physiologically degradable in vivo in a mammal, wherein said carbohydrate-containing polymer comprises a non-naturally occurring hydrophilic, biodegradable polymer unit, a disaccharide or oligosaccharide unit, and a bifunctional spacer linking said disaccharide or oligosaccharide units to said polymer unit, comprising the steps of:

(a) covalently linking a monosaccharide or oligosaccharide unit to a spacer to form a monosaccharide or oligosaccharide-spacer complex wherein said spacer has the formula (mono- or oligosaccharide)—O—[$Q_1$—$(CH_2)_p$—$Q^2$]$_r$-(polymer), wherein $Q^1$ is —$CH_2$ or —CO—, $Q^2$ is —NH or —CO—NH—, p is an integer from 1 to 6, and r is 1 or 2;

(b) covalently linking said monosaccharide or oligosaccharide-spacer complex to a non-naturally occurring hydrophilic, biodegradable polymer unit to form an acceptor unit; and (c) coupling a monosaccharide donor unit to said acceptor unit by enzymatic glycosylation.

2. The process according to claim 1, wherein the enzymatic glycosylation of said acceptor unit takes place in homogeneous aqueous phase.

3. The process according to claim 2, wherein said enzymatic glycosylation of said acceptor is carried out using nucleotide-activated carbohydrates as said monosaccharide donor units and wherein said glycosylation reaction is catalyzed by at least one glycosyltransferase.

4. The process according to claim 1, wherein said glycosylation reaction is carried out at between about pH 6.0 and about pH 8.5.

5. The process according to claim 3, further comprising adding alkaline phosphatase to the reaction medium when said monosaccharide donor unit is added in about equimolar amount or in excess.

6. The process according to claim 3, wherein between about 0.01 to about 10 units of said glycosyltransferase are used.

7. The process according to claim 2, wherein said enzymatic glycosylation is carried out at a temperature between about 10° C. and about 40° C. for between about 1 to about 5 days.

8. The process according to claim 1, wherein polyaminoacid has a molecular weight up to about 70 kD, and is in polyamide or polyanhydride form.

9. The process according to claim 8, wherein said polyamino-acid is selected from the group consisting of poly-α,β-(2-hydroxyethyl)-D,L-aspartamide, poly-D,L-succinimide, polyglutamate, poly-L-lysine methyl ester fumaramide and a copolymer of these polyamino-acids.

10. The process according to claim 1, wherein the linkages connecting the spacer to the monosaccharide or oligosaccharide unit and to the biodegradable polymer unit are formed by reactions selected from the group consisting of alkylation, reductive alkylation, acylation and addition onto a double bond.

11. The process according to claim 1, wherein the disaccharide or oligosaccharide unit of said carbohydrate-containing polymer is selected from the group consisting of: SAα2-6-Galβ1-4-GlcNAc-; SAα2-3-Galβ1-4-GlcNAc-; SAα2-3-Galβ1-3-GlcNAc-; Galβ1-4-(Fucα1-3-GlcNAc-; Galβ1-3-(Fucα1-3)GlcNAc-; SAα2-3-Galβ1-3-(Fucα1-4)GlcNAc-; SAα2-3-Galβ1-4-(Fucα1-3)GlcNAc-, sialyl-Lewis X, sialyl-Lewis A, VIM-2, Lewis A, Lewis B, Lewis X, Lewis Y, Lewis A type$^1$, Lewis A type$^2$, Lewis B type$^1$, Lewis B type$^2$, Lewis H type$^1$ and Lewis H type$^2$.

12. The process according to claim 3, wherein said nucleotide-activated carbohydrate is selected from the group consisting of: UDP-galactose, UDP-glucose, UDP-N-acetylglucosamine, UDP-N-acetyl-galactosamine, UDP-glucuronic acid, CMP-neuraminic acid, GDP-fucose, GDP-mannose, dTDP-glucose and dUDP-galactose.

13. The process according to claim 3, wherein said glycosyltransferase is selected from the group consisting of: β-1,4-galactosyltransferase, Gal-β-1-4-GlcNAc α-2-6-sialyltransferase, Gal-β-1-3-GalNAc α-2-3-sialyltransferase, Gal-β-1-3(4)-GlcNAc α-2-3-sialyltransferase, GalNAc α-2-6-sialyltransferase, N-acetylglucosaminytransferases, α-1-3-fucosyltransferase, α-1-2-fucosyltransferase, α-3/4-fucosyltransferase, and α-1-2-mannosyltransferase.

14. The process according to claim 1, wherein said disaccharide or oligosaccharide unit comprises 2–20 monosaccharide units.

15. A carbohydrate-containing polymer that is physiologically degradable in vivo in a mammal, comprising:

(a) a non-naturally occurring hydrophilic, biodegradable polymer unit, (b) a disaccharide or oligosaccharide unit, and (c) a bifunctional spacer linking said disaccharide or oligosaccharide units to said biodegradable polymer unit, wherein said spacer has the formula (mono- or oligosaccharide)—O—[$Q^1$—$(CH_2)_p$—$Q^2$]$_r$-(polymer), and wherein $Q^1$ is —$CH_2$, or —CO—, $Q^2$ is —NH or —CO—NH—, p is an integer from 1 to 6, and r is 1 or 2.

16. A process for preparing a carbohydrate-containing polymer that is physiologically degradable in vivo in a mammal, wherein said carbohydrate-containing polymer comprises a hydrophilic, biodegradable polymer unit, a disaccharide or oligosaccharide unit, and a bifunctional spacer linking said disaccharide or oligosaccharide units to said polymer unit, comprising the steps of:

(a) covalently linking a hydrophilic, biodegradable polymer unit to a spacer to form a biodegradable polymer-spacer complex wherein said spacer has the formula (mono- or oligosaccharide)—O—[$Q^1$—$(CH_2)_p$—$Q^2$]$_r$-(polymer), wherein $Q^1$ is —$CH_2$ or —CO—, $Q^2$ is —NH or —CO—NH—, p is an integer from 1 to 6, and r is 1 or 2;

(b) covalently linking said biodegradable polymer-spacer complex to a monosaccharide or oligosaccharide unit to form an acceptor unit; and (c) coupling a monosaccharide donor unit to said acceptor unit by enzymatic glycosylation.

17. A process for preparing a carbohydrate-containing polymer that is physiologically degradable in vivo in a mammal, wherein said carbohydrate-containing polymer comprises a non-naturally occurring hydrophilic, biodegradable polyamino-acid, a disaccharide or oligosaccharide unit, and a bifunctional spacer linking said disaccharide or oligosaccharide units to said polymer unit, comprising the steps of:

(a) covalently linking a non-naturally occurring hydrophilic, biodegradable polyamino-acid to a spacer to form a biodegradable polymer-spacer complex, wherein said spacer has the formula (mono- or oligosaccharide)—O—[$Q^1$—($CH_2$)$_p$—$Q^2$]$_r$-(polymer), wherein $Q^1$ is —$CH_2$ or —CO—, $Q^2$ is —NH or —CO—NH—, p is an integer from 1 to 6, and r is 1 or 2;

(b) covalently linking said biodegradable polyamino-acid-spacer complex to a monosaccharide or oligosaccharide unit to form an acceptor unit; and (c) coupling a monosaccharide donor unit to said acceptor unit by enzymatic glycosylation.

* * * * *